United States Patent
Fentress et al.

(10) Patent No.: US 7,214,221 B2
(45) Date of Patent: May 8, 2007

(54) MULTI-STAGE FLUID DELIVERY DEVICE AND METHOD

(75) Inventors: James K. Fentress, Morrisville, NC (US); Kenneth G. Powell, Raleigh, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 485 days.

(21) Appl. No.: 10/396,719

(22) Filed: Mar. 26, 2003

(65) Prior Publication Data
US 2003/0216684 A1 Nov. 20, 2003

Related U.S. Application Data

(60) Provisional application No. 60/367,213, filed on Mar. 26, 2002.

(51) Int. Cl.
*A61K 9/22* (2006.01)

(52) U.S. Cl. ............................... 604/890.1; 604/891.1; 604/134

(58) Field of Classification Search ............ 604/93.01, 604/48, 131–134, 181, 890.1, 891.1, 183–185; 222/92–107; 128/DIG. 12
See application file for complete search history.

(56) References Cited

U.S. PATENT DOCUMENTS

| | | | |
|---|---|---|---|
| 3,814,097 A | 6/1974 | Ganderton et al. | |
| 3,964,482 A | 6/1976 | Gerstel et al. | |
| 4,196,732 A | 4/1980 | Wardlaw | |
| 4,258,711 A | 3/1981 | Tucker et al. | |
| 4,316,463 A | 2/1982 | Schmitz et al. | |
| 4,340,048 A | 7/1982 | Eckenhoff | |
| 4,525,164 A | 6/1985 | Loeb et al. | |
| 4,525,165 A * | 6/1985 | Fischell ...................... 604/131 |
| 4,552,561 A | 11/1985 | Eckenhoff et al. | |
| 4,734,092 A | 3/1988 | Millerd | |
| 4,772,263 A | 9/1988 | Dorman et al. | |
| 4,781,688 A | 11/1988 | Thoma et al. | |
| 4,886,499 A | 12/1989 | Cirelli et al. | |
| 4,921,475 A | 5/1990 | Sibalis | |

(Continued)

FOREIGN PATENT DOCUMENTS

DE 4039191 C1 11/1991

(Continued)

OTHER PUBLICATIONS

PCT Search Report for PCT/US03/09021.

*Primary Examiner*—Kevin C. Sirmons
*Assistant Examiner*—Benjamin Huh
(74) *Attorney, Agent, or Firm*—Robert E. West

(57) ABSTRACT

A fluid delivery device for delivering a substance to a patient by way of infusion delivers the preparation at a rate of flow which varies in steps from a substantially constant higher rate, to a stepped-down substantially constant lower rate or rates. The delivery device includes one or more reservoirs, and one or more Belleville springs for applying generally constant pressures to the substance contained in the reservoirs. Each reservoir will have a different constant pressure applied in a mid-range of operation. The reservoirs can be interconnected to each other and to an infusion device in a number of arrangements, including various manifolds and flow restrictors, such that the rate of flow is controlled in steps in accordance with the pressures applied by the springs of the plurality of reservoirs.

19 Claims, 8 Drawing Sheets

U.S. PATENT DOCUMENTS

| | | |
|---|---|---|
| 5,011,477 A | 4/1991 | Winchell et al. |
| 5,045,064 A | 9/1991 | Idriss |
| 5,090,963 A | 2/1992 | Gross et al. |
| 5,250,023 A | 10/1993 | Lee et al. |
| 5,279,544 A | 1/1994 | Gross et al. |
| RE35,192 E | 3/1996 | Reese |
| 5,554,131 A | 9/1996 | Lacivita |
| 5,649,910 A | 7/1997 | Kriesel et al. |
| 5,656,032 A | 8/1997 | Kriesel et al. |
| 5,665,070 A | 9/1997 | McPhee |
| 5,693,018 A | 12/1997 | Kriesel et al. |
| 5,716,343 A | 2/1998 | Kriesel et al. |
| 5,848,990 A | 12/1998 | Cirelli et al. |
| 5,858,001 A | 1/1999 | Tsals et al. |
| 5,858,005 A | 1/1999 | Kriesel |
| 5,885,250 A | 3/1999 | Kriesel et al. |
| 5,921,962 A | 7/1999 | Kriesel et al. |
| 5,957,895 A | 9/1999 | Sage et al. |
| 5,961,492 A | 10/1999 | Kriesel et al. |
| 5,997,501 A | 12/1999 | Gross et al. |
| 6,074,369 A | 6/2000 | Sage et al. |
| 6,099,504 A | 8/2000 | Gross et al. |
| 6,132,755 A | 10/2000 | Eicher et al. |
| 6,186,982 B1 | 2/2001 | Gross et al. |
| 6,500,150 B1 | 12/2002 | Gross et al. |
| 6,589,229 B1 | 7/2003 | Connelly et al. |
| 6,595,956 B1 | 7/2003 | Gross et al. |
| 6,611,707 B1 | 8/2003 | Prausnitz et al. |
| 6,656,147 B1 | 12/2003 | Gertsek et al. |
| 6,702,779 B2 | 3/2004 | Connelly et al. |
| 6,780,171 B2 | 8/2004 | Gabel et al. |
| 2001/0056259 A1* | 12/2001 | Skinkle et al. .............. 604/151 |
| 2002/0055711 A1 | 5/2002 | Lavi et al. |
| 2002/0095134 A1 | 7/2002 | Pettis et al. |
| 2003/0045837 A1 | 3/2003 | Delmore et al. |
| 2003/0109827 A1 | 6/2003 | Lavi et al. |
| 2003/0187394 A1 | 10/2003 | Wilkinson et al. |
| 2003/0187423 A1 | 10/2003 | Wilkinson et al. |
| 2003/0208167 A1 | 11/2003 | Prausnitz et al. |
| 2004/0138612 A1 | 7/2004 | Shermer et al. |
| 2005/0065466 A1 | 3/2005 | Vedrine |
| 2005/0065472 A1 | 3/2005 | Cindrich et al. |

FOREIGN PATENT DOCUMENTS

| | | |
|---|---|---|
| WO | WO 95/13838 | 5/1995 |
| WO | WO 97/21457 | 6/1997 |

* cited by examiner

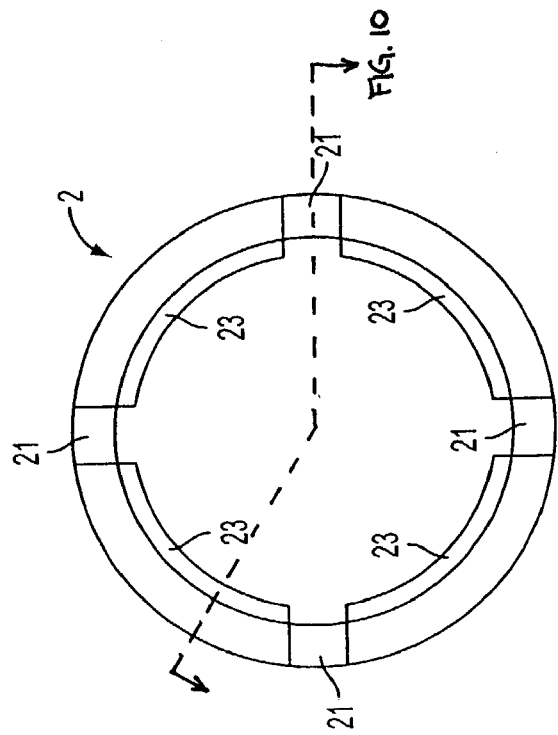
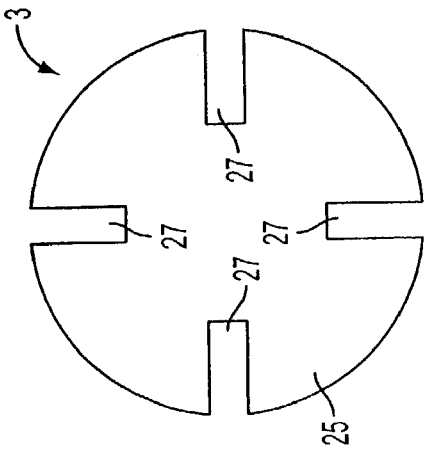
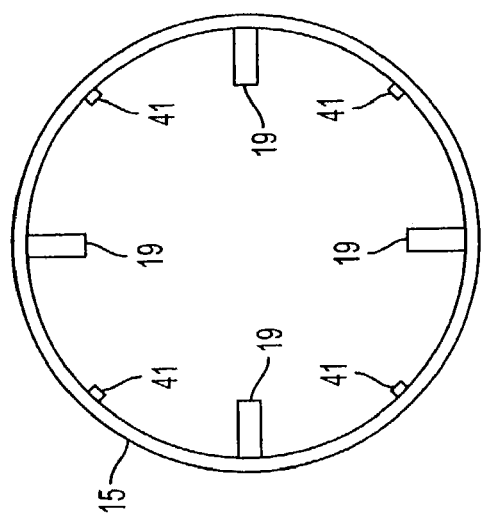
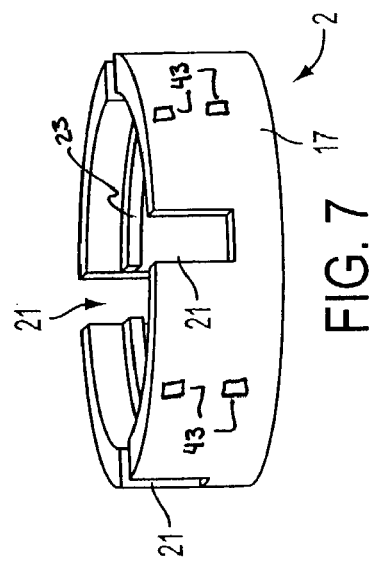

MULTI-STAGE FLUID DELIVERY DEVICE AND METHOD

This application claims the benefit under 35 U.S.C. §119 (e) of U.S. provisional patent application Serial No. 60/367,213, entitled "Multi-Stage Fluid Delivery Device", filed Mar. 26, 2002, the entire contents of which are incorporated herein by reference.

FIELD OF THE INVENTION

The present invention relates to a system and method using fluid delivery devices to deliver a substance, for example, a therapeutic fluid material, to a patient by infusion, and more particularly, to a device in which the flow rate is automatically adjusted from an initial high rate to one or more stepped-down lower flow rates.

BACKGROUND OF THE INVENTION

When medicinal doses are delivered to patients by infusion, it is sometimes desirable to deliver the medicinal dose at an initially high rate and then deliver the remaining dose at one or more stepped-down lower rates. For example, it is typically desirable for an initial flow for drug infusion to be substantially higher than the desired therapeutic rate, so as to rapidly increase the blood concentration into the desired therapeutic range. This initial high rate of flow is called the "bolus rate". Once the drug concentration has been increased into the therapeutic range, the flow rate is dropped to the rate necessary to maintain the concentration of the drug in the therapeutic range. This latter flow rate is called the "basal rate".

Prior to the present invention described below, to achieve a stepped adjustment of the flow rate automatically, an infusion device with an electronically-controlled pump was required. Accordingly, there is a need for a non-electronic infusion device of a simple mechanical construction which does not require a pump, and which can automatically deliver drugs to a patient by way of infusion at an initial high infusion rate, followed by one or more stepped-down lower infusion rates.

SUMMARY OF THE INVENTION

A drug delivery apparatus, according to the present invention, comprises a non-electronic, ambulatory, disposable system that provides, during a delivery operation, at least one step decrease in flow rate of a fluid under pressure from a reservoir system. The pressure on the fluid is provided by at least one constant force spring acting on the fluid in at least one of the reservoirs. The fluid, under pressure, passes through a flow restrictor on its way to any number of suitable patient delivery devices, such as a needle device or catheter.

Different spring forces are applied to the reservoir system. In the illustrated embodiments, at least one constant force spring is associated with each of the reservoirs, each constant force spring applying a force different from the constant force applied by one or more other constant force springs. In the illustrated embodiments, the constant force springs are Belleville springs.

The present invention is especially useful with needles, particularly microneedles, having ports in their sides.

BRIEF DESCRIPTION OF THE DRAWINGS

FIG. 6 is a bottom plan view of the upper portion of the housing of the apparatus shown in FIGS. 4 and 5;

FIG. 7 is a perspective view of the bottom portion of the housing of the apparatus shown in FIGS. 4 and 5;

FIG. 8 is a top plan view of the bottom portion of the housing shown in FIG. 7;

FIG. 9 is a top plan view of a shelf used to support a reservoir in the apparatus shown in FIGS. 4 and 5;

DESCRIPTION OF THE PREFERRED EMBODIMENTS

The embodiments of the present invention described below include an infusion device of a simple mechanical construction which does not require a pump, and which can automatically deliver drugs to a patient by way of infusion at an initial high infusion rate, followed by one or more stepped-down lower infusion rates. While the primary application of the invention will be to provide only two rates of flow, there are many applications in which several different flow rates may be desirable such as, for example, when the desired or target therapeutic rate decreases with time. In order to facilitate control of the rate of flow as well as the amount of drug delivered at the various rates, both the initial high rate of drug flow, as well as the one or more stepped-down rates of flow, are substantially constant.

Figure 1:
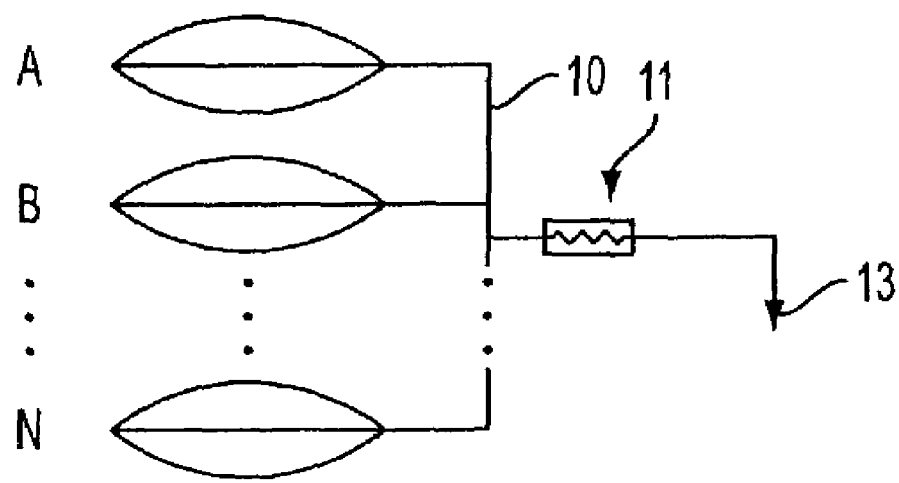
FIG. 1 schematically illustrates a multi-stage fluid delivery device for delivering fluids to a patient by infusion in accordance with an embodiment of the present invention.

In the fluid delivery device shown in FIG. 1, a plurality of reservoirs "A" through "N" are provided. Each reservoir includes at least one spring for applying pressure to the fluid contained in the reservoir. In the preferred embodiment, the reservoir "A" will include a spring to apply the greatest constant pressure to the contained fluid, and each of the remaining reservoirs "B" through "N" will apply progressively lower constant pressures to the fluids contained therein. As shown in FIG. 1, the outlets from the reservoirs "A" through "N" are connected with each other through a common fluid connection or manifold comprising flow line 10, and are connected through a common flow restrictor 11 to an infusion device 13, which may be a needle or an array of needles.

Figure 3:
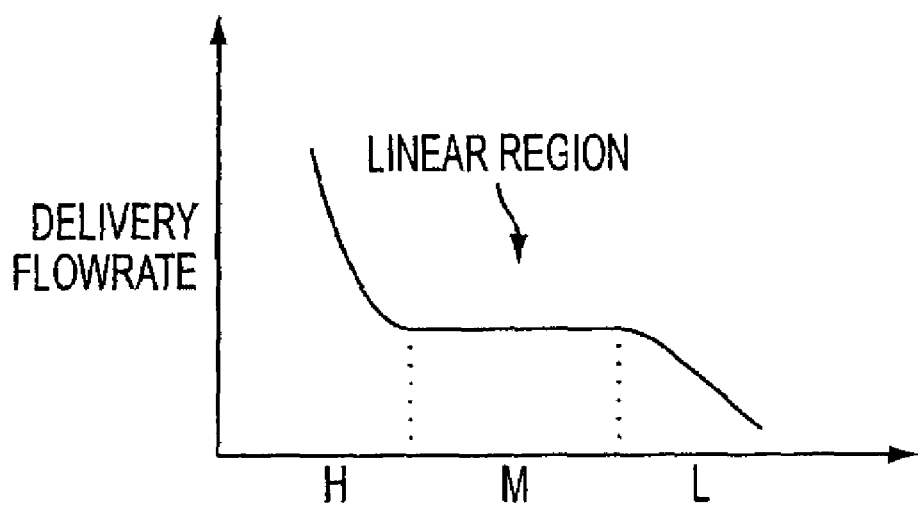
FIG. 3 illustrates the delivery flow rate from a reservoir of the type employed in an embodiment of the present invention plotted against the displacement of the constant force spring.

In the preferred embodiment, each of the reservoirs "A" through "N" is provided with at least one spring, which when actuated, will apply a force to the reservoir and pressurize the fluid contained therein. As shown in FIG. 3, the springs of each reservoir are designed to apply a substantially constant pressure to the fluid within the reservoir over a mid-range of operation as the fluid flows out of the reservoir. FIG. 3 illustrates the rate of flow from a reservoir plotted against the displacement of the spring pressurizing the reservoir.

In FIG. 3, in region "L" at low levels of spring displacement, the flow rate increases and decreases as the displacement of the spring against the reservoir increases and decreases. In region "H" at high levels of spring displacement, the flow rate increases and decreases as the displacement of the spring increases and decreases. Between the two regions "L" and "H" is the mid-range "M" of operation of the reservoir and the flow rate is maintained substantially constant as the displacement of the reservoir changes. The pressure within the reservoir is directly proportional to the flow rate. Accordingly, the curve shown in FIG. 3 also corresponds to the pressure within the reservoir plotted against the displacement of the spring, and shows that the pressure on the fluid remains substantially constant through the mid-range "M" of operation. The amount of fluid in a reservoir corresponds to the spring displacement for that reservoir. Thus when a reservoir is operating in a mid-range "M" as shown in FIG. 3 and fluid flows out of the reservoir, the spring displacement will decrease while applying a substantially constant pressure to the contained fluid, causing the fluid to flow out of the reservoir at a substantially constant rate until the spring displacement moves into the region "L".

In the preferred embodiment, one of the reservoirs, for example reservoir "A", in the system of FIG. 1, has a spring which applies the greatest spring pressure to the contained fluid in the mid-range "M" of reservoir operation and this reservoir initially will be filled with fluid to be in this mid-range. Each of the remaining reservoirs "B" through "N" will apply progressively lower pressures to the contained fluids in their mid-ranges M.

Returning to FIG. 1, when the reservoirs "A" through "N" are initially actuated to apply pressure to their contained fluids, the pressure in reservoir "A" will be transmitted to the reservoirs "B" through "N" through the fluid connection 10. As a result, the reservoirs "B" through "N" will be hyper-inflated to region "H" as shown in FIG. 3. With this arrangement, the therapeutic preparation flows first out of the reservoir "A" through the flow restrictor and out through the infusion device 13 to the patient. The high back pressure provided by the reservoir "A" to the reservoirs "B" through "N" will initially prevent any substantial flow from occurring from the reservoirs "B" through "N" to the infusion device. As a result, the flow rate through the infusion device will be controlled to be at a high constant rate in accordance with the spring pressure provided by the spring of the reservoir "A".

Figure 2:
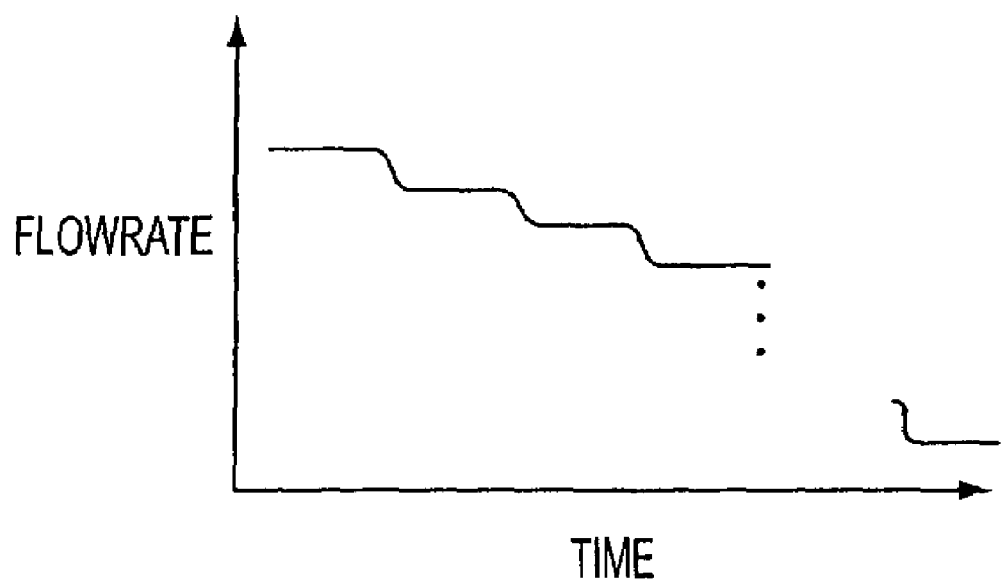
FIG. 2 shows a graph of the flow rate versus time provided by the system shown in FIG. 1.

As the reservoir "A" empties, the spring of the reservoir "A" will eventually contract into the non-constant flow rate region "L", as shown in FIG. 3. At this point of the operation, most of the fluid will have been dispensed from the reservoir "A". The drop in pressure in the reservoir "A" transmitted to the reservoir "B" will cause the reservoir "B" to transition from the region "H" shown in FIG. 3 into the constant flow rate region "M", whereupon the flow from the second reservoir "B" to the infusion device will be at a substantially constant rate as the spring of the reservoir "B" contracts. During this period, with the flow from the reservoir "B" substantially constant, there will be still some flow from the reservoir "A", but the flow from reservoir "A" will be less than 1% of the total volume of flow of the system and most of the flow will be at the substantially constant rate determined by the spring pressure applied to the contained fluid of reservoir "B". In this manner, a constant stepped-down level of flow is achieved. The pressure in the reservoir "B" in the mid-range "M" will be transmitted to the remaining reservoirs of the system to maintain the remaining reservoirs hyper-inflated and prevent any substantial flow from the remaining hyper-inflated reservoirs. The transition of an outflow coming from reservoir "B" to an outflow coming from the remaining reservoirs will occur in the same manner as described above in connection with the transition from reservoir "A" to reservoir "B", and as a result the system achieves a stepped flow rate with time as shown in FIG. 2.

As described above, the system of the invention may comprise more than two reservoirs, but in the most useful application of the invention, only two flow rates are needed, in which case, the system of FIG. 1 would be implemented with only two reservoirs, "A" and "B". However, any number of reservoirs, and reservoir configurations can be included to create a desired stepped delivery profile.

Figure 4:
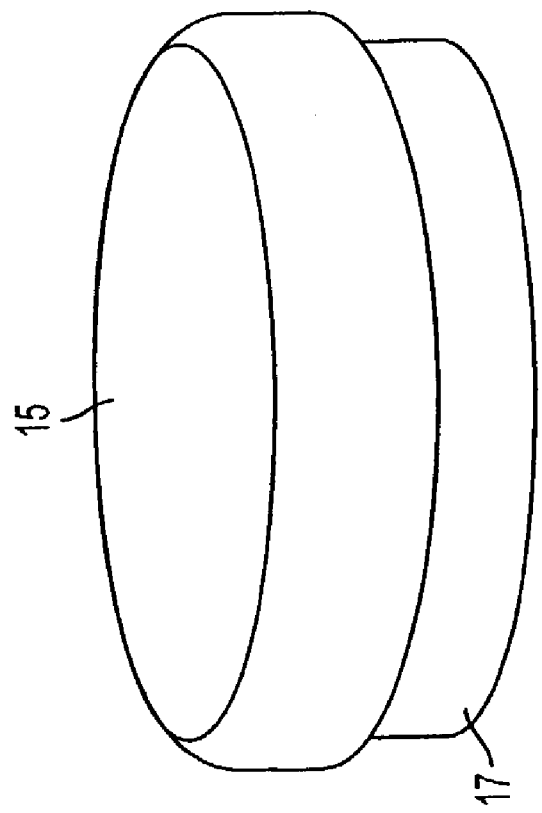
FIG. 4 is perspective view of an apparatus in accordance with an embodiment of the present invention in an unactuated state.

In accordance with the preferred embodiment of the invention, the reservoirs are contained in a housing as shown in FIGS. 4 through 10. The apparatus has a stable unactuated state as shown in FIG. 4 and an actuated state shown in FIG. 5. The apparatus comprises an upper housing portion 15 and a lower housing portion 17. To actuate the apparatus from the unactuated state shown in FIG. 4 to the actuated state shown in FIG. 5, the upper and lower housing portions 15 and 17 are compressed together to the state shown in FIG. 5. The upper housing portion 15, as shown in FIG. 6, is provided with tabs 19 which extend radially inward from the bottom edge of the upper housing portion 15. In the assembled device, the tabs 19 fit in slots 21 defined in the cylindrical side wall of the lower housing portion 17. Between the slots 21, ledges 23 extend radially inward from the inner wall of the lower housing portion 17 as shown in FIG. 8. Ledges 23 support a shelf 25 which is shown in FIG. 9. The shelf 25 is provided with slots 27 extending radially inward and the shelf is positioned in the lower housing portion 17 with the slots 27 aligned with the slots 21 in the wall of the lower housing portion 17.

Figure 10:
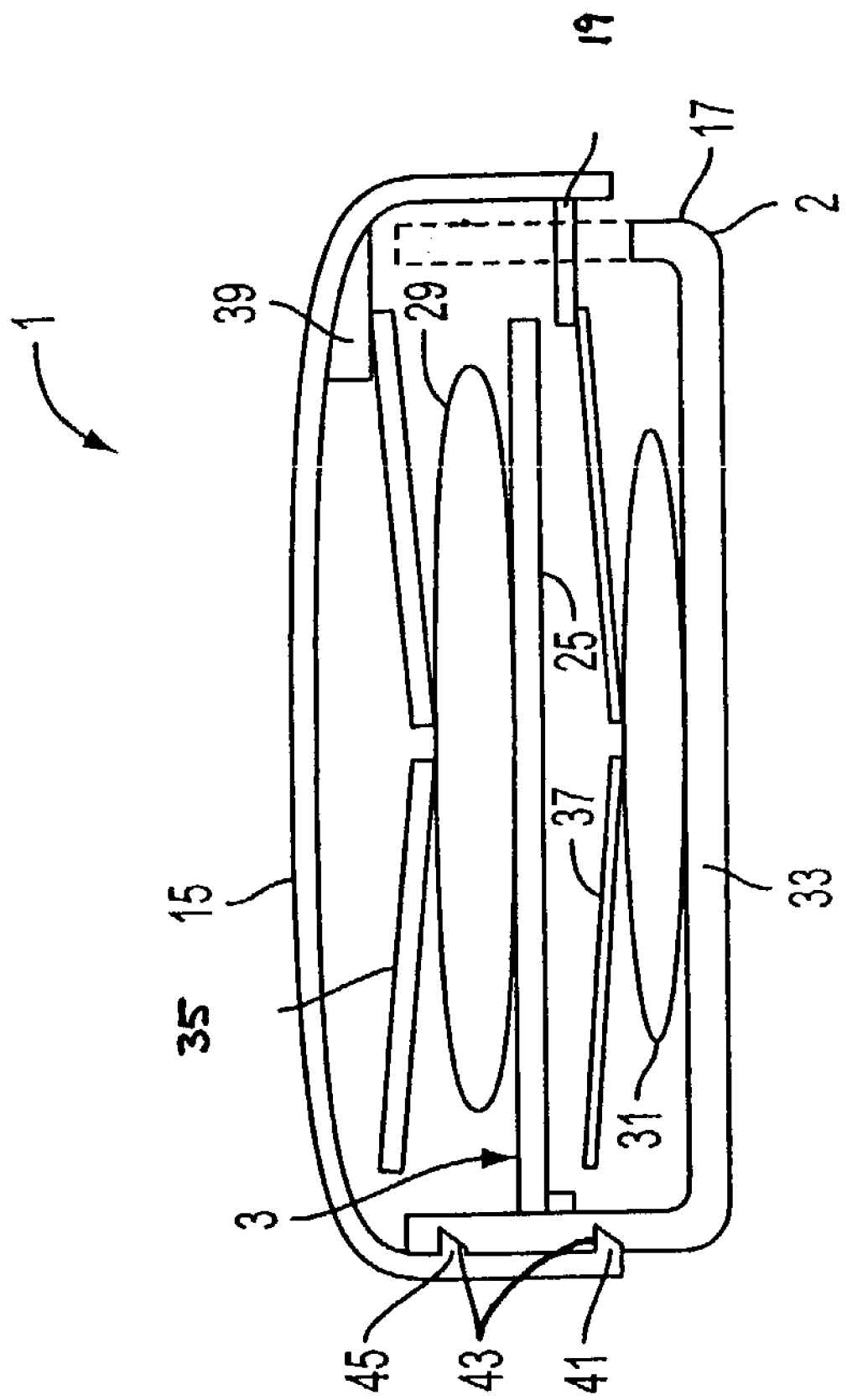
FIG. 10 is a sectional view of the apparatus shown in FIGS. 4 and 5 in the process of being actuated.

The sectional view of the apparatus shown in FIG. 10 is taken along different vertical planes extending from the vertical axis of the housing through the sidewalls of the housing as indicated in a view line shown in FIG. 8. FIG. 10 is a sectional side view of an assembled embodiment of the present invention, where the right side of the sectional view of FIG. 10 extends through one of the slots 21, and the left side of the sectional view of FIG. 10 extends through one of the ledges 23. As shown in FIG. 10, a reservoir 29 is supported on the shelf 25 and a reservoir 31 is supported on a bottom wall 33 of the lower housing portion 17.

A first spring, such as a Belleville spring 35, is provided in the housing in the space between the reservoir 29 and the upper housing portion 15 and is adapted to engage the reservoir 29 when the apparatus is actuated. A second Belleville spring 37 is provided in the housing between the reservoir 31 and the shelf 25, and is adapted to engage the reservoir 31 when the apparatus is actuated.

Wedge shaped bosses 39 are provided on the underside of the top wall of the upper housing portion 15 positioned to engage the radially outer section of the top surface of the spring 35 when the apparatus is actuated and to force the spring 35 into engagement with the reservoir 29. There are four of the bosses 39, which are positioned at 90° intervals around the spring 35. The tabs 19 engage the radially outer section of the top surface of the spring 37 when the apparatus is being actuated to force the spring 37 in engagement with the reservoir 31.

Wedge shaped detents 41 extend radially inward from the bottom edge of the inner surface of the sidewalls of the housing upper portion 15 and are lodged in complementary shaped recesses 43 in the outer surface of the sidewall of the housing lower portion 33 when the apparatus is unactuated, and hold the apparatus stably in the unactuated state. The detents 41 slope inwardly from the bottom edge so that they easily slide out of the recesses 43 when the upper and lower housing portions 15 and 17 are compressed together.

A second set of detents 45 are provided on the inner sidewall of the upper housing portion 15 above and vertically aligned with the detents 41 and are adapted to lodge in the recesses 43 when the apparatus is compressed fully to the actuated state. The detents 45 upon lodging in the recesses 43 will hold the apparatus in the actuated state so as to prevent the apparatus from popping back to the unactuated state and prevent reuse of the apparatus.

When the device is actuated both of the springs 35 and 37 will undergo displacement from their unstressed state. One of the springs, for example the spring 35, will be displaced into its operating region "M" and apply a constant force to the fluid in the reservoir 29. The pressure in the reservoir 29 will be transmitted to the fluid in the reservoir 31 by the fluid connection between the reservoirs and cause the spring 37 to be displaced into its operating region "H". Each reservoir shown generally at 29 and 31, includes at least one fluid connection that connects the reservoirs to a manifold which connects to an infusion device. In the embodiment shown, the manifold can contain a flow restrictor located between the manifold and the infusion device. The infusion device could be a needle which is hidden when the apparatus is unactuated and which is driven into the skin of the patient when the apparatus is actuated.

The resulting apparatus will produce a stepped rate of flow from a high rate to a low rate in the manner described above in connection with FIG. 1. The apparatus shown in FIGS. 4 through 10 can be extended to include any number of reservoirs and springs in the stack of reservoirs. In the preferred embodiment all the springs in the apparatus are compressed at once when the apparatus is actuated. However, in another embodiment of the present invention, it is possible to have additional sets of tabs so arranged to actuate the springs in stages with successive detents provided, and with the apparatus actuated successively between stages by increased pressure applied to compress the housing. In such arrangements multiple drug infusion and/or multiple delivery rates could be carried out.

Figure 15:
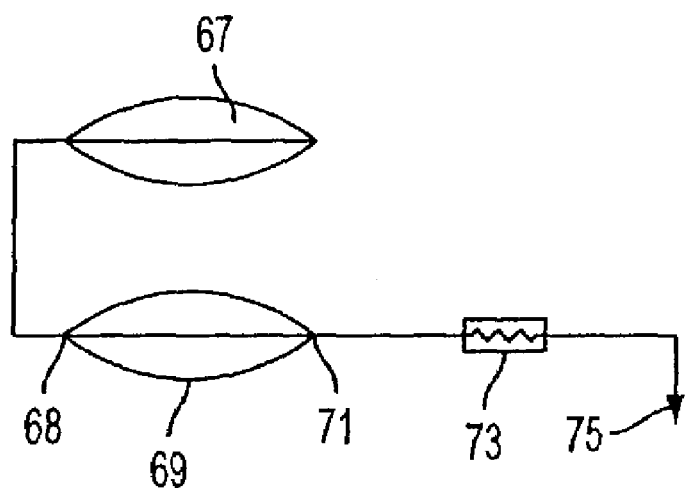
FIG. 15 illustrates yet another alternative embodiment of a fluid infusion device in accordance with the present invention for mixing two different therapeutic preparations during infusion while providing an automatic step-down in the flow rate.
Figure 5:
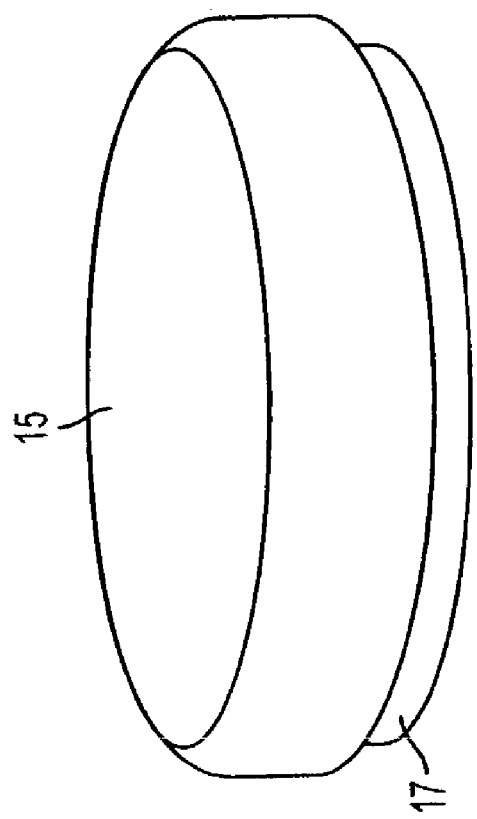
FIG. 5 illustrates a perspective view of the apparatus of FIG. 4 in an actuated state.

In the above described systems, the reservoirs are connected to a common output connection or manifold as shown in FIG. 1. The pressure applied to each of the reservoirs is immediately transmitted to the other reservoirs and as a result, the pressure in all of the reservoirs will be equalized. Thus, the plurality of reservoirs may be considered a reservoir system which applies the same pressure to the fluid contained by the reservoir system. In another embodiment of the present invention, each reservoir, or subgroup of reservoirs, can be separately connected via a separate flow restrictor to an infusion device as shown in FIG. 13. Reservoirs, or subgroups of reservoirs can also be connected in series as shown in FIG. 15. In still another embodiment of the present invention, the reservoir system, instead of being a plurality of reservoirs, could be a single reservoir with a plurality of springs having different mid-ranges of operation where the springs apply different constant pressures to the fluid contained in the reservoir system as shown in FIGS. 11 and 12.

Figure 11:
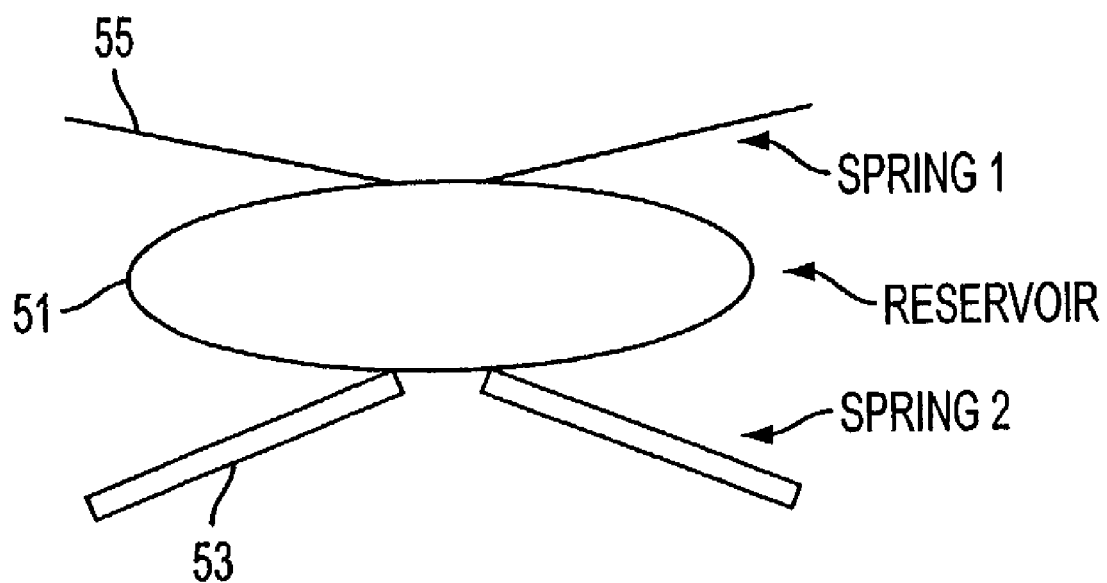
FIG. 11 schematically illustrates an alternative embodiment of a fluid infusion device in accordance with the present invention employing only one reservoir in an unactuated state.
Figure 12:
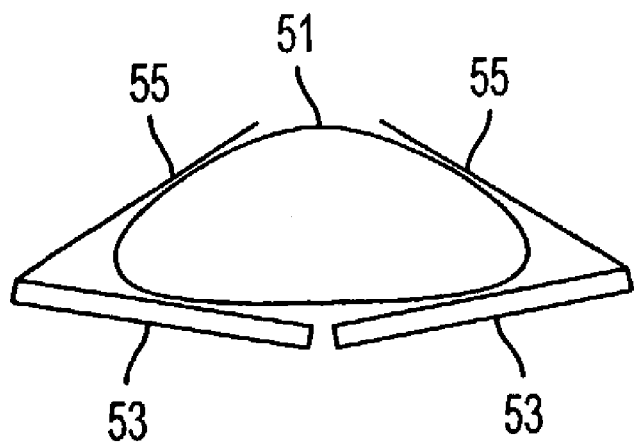
FIG. 12 schematically illustrates the embodiment of FIG. 11 in an actuated state.
Figure 13:
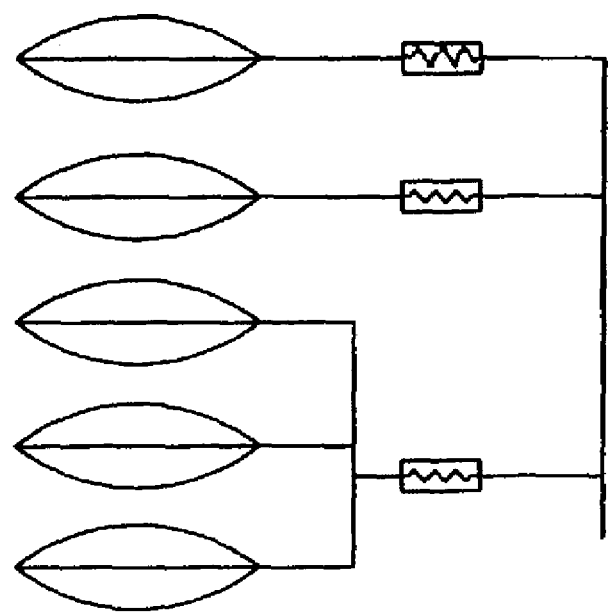
FIG. 13 illustrates another alternative embodiment of a fluid infusion apparatus in accordance with the present invention.

The embodiment of the invention illustrated in FIGS. 11 and 12 comprises such a system, in which a single reservoir is designed to deliver a therapeutic fluid to an infusion device at an initially high constant rate, which then steps down to a lower constant rate. FIGS. 11 and 12 illustrate the reservoir and spring configuration of the embodiment, wherein the housing is substantially as described above. As shown in FIG. 11, the system comprises a single reservoir 51 which is acted upon by Belleville springs 53 and 55 applying pressure to the reservoir SI from opposite sides. FIG. 11 shows the system in an unactuated state.

When the system is actuated, the springs 53 and 55 are compressed to engage and apply forces to the reservoir. Upon actuation, the spring 53 is compressed into a mid-range "M", and spring 55, having a different response characteristic, is forced into a high range "H" of operation. In this mid-range, the spring 53 is designed to apply greater force to the reservoir than the spring 55. As a result, the fluid within the reservoir 51 will be pressurized in accordance with the force applied to the reservoir by the spring 53, and the spring 55 will be displaced to its non-constant force region "H".

When the device is actuated as shown in FIG. 12, the fluid will flow out of the reservoir 51 at a constant rate determined by the spring 53, whereupon the spring 53 will pass from the region "M" into the region "L" of FIG. 3, and the spring 55 will pass from the region "H" into the region "M". The rate flow from the reservoir 51 will then be controlled to be at a lower constant rate determined by the spring 55, whereupon the spring 55 will pass from the region "M" into the region "L" of FIG. 3, and flow will substantially cease. Thus, in this manner, the system provides a stepped rate of flow starting with an initial high constant rate, and then stepping down to a lower constant rate until complete.

Figure 14:
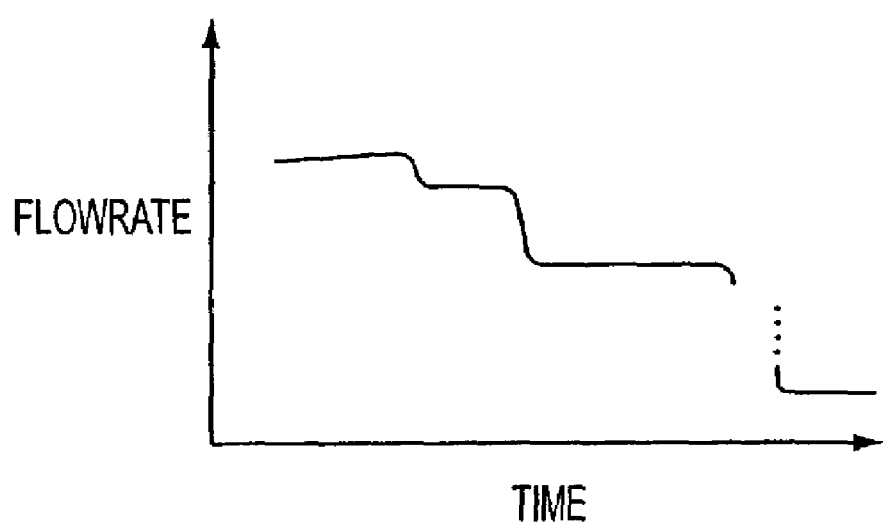
FIG. 14 illustrates the flow rate versus time provided by the embodiment of FIG. 13.

In yet another embodiment of the present invention, instead of connecting the reservoirs through a common flow restrictor, each reservoir could be connected to the infusion device through separate flow restrictors. Some of the reservoirs may be arranged to connect to the infusion device through a common flow restrictor, while other reservoirs are connected to the infusion device through separate flow restrictors as shown in FIG. 13. The degree of flow restriction provided by the flow restrictors and the stiffness of each individual spring may be varied to tune the system to achieve the desired variation in flow rate with time. FIG. 14 shows a flow rate variation provided by the system of FIG. 13.

FIG. 15 shows still another embodiment of the present invention and an arrangement of the reservoirs and their interconnection with the infusion device. As shown in FIG. 15, the outlet of a reservoir 67 is connected to an inlet 68 of a reservoir 69, which is provided with an outlet 71 on the opposite side of the reservoir 69 from the inlet 68. The outlet 71 is connected through a flow restrictor 73 to an infusion device 75. In the arrangement of FIG. 15, the reservoir 67 is provided with the stronger spring to exert the greatest constant pressure on the contained fluid, whereby the reservoir 69 will be hyper-inflated. With this arrangement, the therapeutic preparation within the reservoir 67 will flow into the reservoir 69 and mix with the therapeutic preparation in the reservoir 69 and the mixed therapeutic preparations will flow from the reservoir 69 through the flow restrictor 73 and the infusion device 75 to the patient at a constant flow rate determined by the spring of the reservoir 67.

When the reservoir 67 empties sufficiently to pass into the region "L" as shown in FIG. 3, the flow rate will drop to that controlled by the spring of reservoir 69, and the mixture of the two therapeutic preparations will continue to flow from the reservoir 69 through the infusion device 75 to the patient. The continued flow at the lower constant rate will be, a mixture of the two therapeutic preparations because the therapeutic preparation in the reservoir 67 will mix with the therapeutic preparation in the reservoir 69 as it flows into the reservoir 69, and the preparations will remain mixed in the reservoir 69 when the flow from the reservoir 67 drops off, as it passes into the region "L". Through judicious choice of springs, variations in therapeutic mixture composition can be achieved and delivered.

The arrangement of FIG. 15 is used to inject a mixture of therapeutic preparations which are not compatible with one another, preventing their being stored in a mixed state. If the delivery time is sufficiently short relative to the pharmacokinetic clearance time, the limited mixing of the pharmaceutical preparations during delivery will not affect either of the pharmaceutical preparations.

Figure 16:
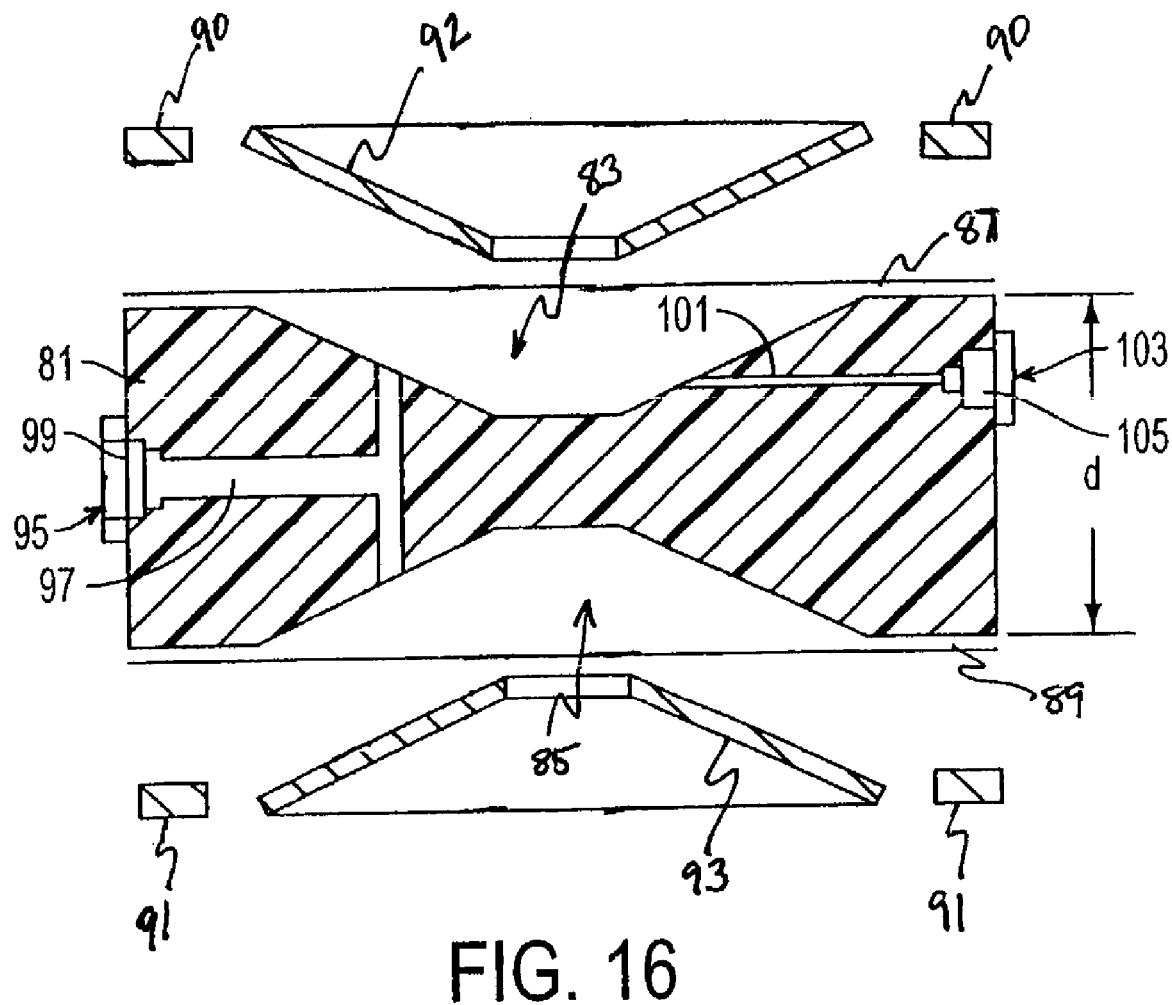
FIG. 16 is a schematic exploded sectional view of yet another embodiment of a fluid infusion device in accordance with the present invention.

In still another embodiment of the present invention shown in FIG. 16, a main body 81 has recesses 83 and 85 formed in the upper and lower surfaces thereof. The recesses 83 and 85 are in the forms of truncated cones recessed in the upper and lower planar surfaces of the body 81. An upper film 87 closes the upper recess 83 and a lower film 89 closes the lower recess 85 to define upper and lower reservoirs. The films 87 and 89 are bonded to the upper and lower planar surfaces of the main body 81 around the edges of the recesses 83 and 85 by adhesive. In addition, the films 87 and 89 are preferably mechanically held in position on the upper and lower surfaces of the main body 81 by means of retaining rings 90 and 91, respectively. Belleville springs 92 and 93 are arranged to engage and apply spring forces to the films 87 and 89, and to the upper and lower reservoirs enclosed in the recesses 83 and 85 by the films 87 and 89.

As shown in FIG. 16, the main body 81 further defines a fill-port 95 in the sidewall thereof. The fill-port 95 is connected by a fluid connection 97 to the upper and lower reservoirs, that is, the reservoirs created by the films 87 and 89 covering recesses 83 and 85, respectively. The fill-port 95 is connected by the fluid connection, with the fluid connection defining one type of manifold usable in connection with the present invention. The fill-port 95 can then be closed by a septum 99.

In addition, the upper reservoir is connected by a fluid connection 101 to an outlet port 103, which is closed by septum 105. The fluid connection 101 defined in the body 81 can be made small enough to serve as a flow restrictor for fluid being dispensed from the reservoir. The septums 99 and 105 are self sealing and provide methods of introducing and dispensing fluid from the reservoirs of the device. The septums may be rubber or silicone, needle-puncturable membranes, or they may be more complex valve systems.

In operation the reservoirs of the device are filled through the fill-port 95 causing the film members 87 and 89 to inflate and engage the springs 92 and 93. This action causes the springs to be stressed so that they apply forces to the fluid contained in the reservoirs. As in the other embodiments described above, the spring forces applied by the two springs in their mid-ranges of operation may be different. For example, the spring 93 may be the stronger spring, such that when spring 93 is displaced to its mid-range of operation, the spring 92 is displaced to the region "H". As a result, fluid will be dispensed through the outlet fluid connection 101 to an infusion device at a high constant initial rate controlled by the spring 93 and thereafter at a stepped down lower rate controlled by the spring 92.

The apparatus of FIG. 16 is advantageous over prior art designs because it provides a way of doubling the drug capacity of the device without resorting to the use of larger springs. In addition, the device is in the form of a sealed, conveniently modular, drug-filled disk. Moreover, it provides a convenient and compact way for a flow restrictor to be implemented in the fluid pathway from the reservoirs to the infusion device. By employing the main body 81 between the springs of the device, a full range of motion of both springs can be utilized, effectively doubling the delivery capacity of the device without substantially increasing its size.

In still another embodiment, if separate fill ports are provided for each of the reservoirs and a separate fluid connection is provided between the two reservoirs, the upper and lower reservoir may be filled with different therapeutic preparations to be mixed upon infusion. The therapeutic preparation in the lower reservoir with the stronger spring will flow into and mix with the therapeutic preparation in the upper reservoir and the mixed therapeutic preparations will flow through the infusion device to the patient as described in connection with the embodiment of FIG. 15. The apparatus of FIG. 16 thus provides a convenient efficient apparatus for carrying out the concept of the invention illustrated in FIG. 15.

As described above the springs in the embodiment of FIG. 16 are put under stress by filling the reservoirs causing the films 87 and 89 to expand to engage and displace the springs 92 and 93. Alternatively, the upper and lower reservoirs could be filled without being placed under pressure and the pressure applied to the reservoirs when the apparatus is actuated by compressing the upper and lower housing portions to force the springs 92 and 93 into engagement with the films as described in connection with the embodiment of FIGS. 4 through 10.

As described above, the system of the present invention provides a delivery system for delivering a therapeutic preparation to a patient by way of infusion, wherein the rate of flow of the therapeutic preparation to the patient is carried at an initially high, generally constant rate, and then is stepped down to one or more lower rates. The device achieves this flow rate control with a simple mechanical construction without the need of pumps or electronics.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A fluid delivery device for delivering a substance to a patient at an increment variable flow rate, comprising:
   an upper housing portion, having an upper housing body extending along a longitudinal axis between a distal and proximal end, and comprising a first chamber therein, said upper housing body having a first opening at said distal end accessing said first chamber;
   a lower housing portion slidably positioned within said first opening of said upper housing portion, said lower housing portion having a lower housing body extending along a longitudinal axis between a distal and proximal end, and comprising a second chamber therein, said lower housing body having a second opening at said proximal end accessing said second chamber;
   a plurality of springs, wherein each spring of said plurality includes a high, low, and mid-range of operation, and wherein at least one spring is a constant force spring adapted for application of a substantially constant pressure through said mid-range of operation of said at least one spring, and wherein said plurality of springs are positioned within at least one of said first and second chambers wherein: said second chamber comprises an inner and an outer surface and a first plurality of slots extending between said inner surface and said outer surface; and
   a ledge extending from said inner surface of said second chamber and having a second plurality of slots aligned with said first plurality of slots;
   at least one infusion device; and
   at least one reservoir in fluid communication with said at least one infusion device, said reservoir being positioned adjacent to at least one of said plurality of springs.

2. A fluid delivery device as claimed in claim 1 further comprising at least one flow restrictor.

3. A fluid delivery device as claimed in claim 1 wherein said constant force spring is a Belleville spring.

4. A fluid delivery device as claimed in claim 1 further comprising: a shelf, positioned adjacent to said ledge and having a third plurality of slots aligned with said first and second plurality of slots.

5. A fluid delivery device as claimed in claim 4 wherein: said first chamber comprises an inner and an outer surface and having a plurality of tabs extending from said inner surface, said plurality of tabs aligned with said first, second, and third plurality of slots.

6. A fluid delivery device as claimed in claim 5 wherein: said tabs are slidable within said first, second, and third slots between an unactuated and an actuated position, and said plurality of tabs engage at least one of said plurality of springs in said actuated position.

7. A fluid delivery device as claimed in claim 6 wherein: said engaged spring is flexed into at least one of a mid-range and a high-range of operation, and said spring in said mid-range of operation transfers a substantially constant pressure to said adjacent reservoir and forces a substance from said reservoir at a first substantially constant flow rate.

8. A fluid delivery device as claimed in claim 5 further comprising a plurality of bosses extending from said inner surface of said first chamber, wherein said bosses engage at least one of said plurality of springs in an actuated position.

9. A fluid delivery device as claimed in claim 8 wherein: said engaged spring is flexed into at least one of a mid-range and a high-range of operation, wherein said spring in said mid-range of operation transfers a substantially constant pressure to said adjacent reservoir and forces a substance from said reservoir at a second substantially constant flow rate.

10. A fluid delivery device as claimed in claim 5 further comprising: at least one unactuated locking detent and at least one actuated locking detent, each of said detents extending from said inner surface of said first chamber and slidably contacting said outer surface of said second chamber; and at least one unactuated locking recess and at least one actuated locking recess, each said recesses disposed on said outer surface of said second chamber.

11. A fluid delivery device for delivering a substance to a patient at an increment variable flow rate, comprising:
    an upper housing portion, having an upper housing body extending along a longitudinal axis between a distal and proximal end, and comprising a first chamber therein, said upper housing body having a first opening at said distal end accessing said first chamber;
    a lower housing portion slidably positioned within said first opening of said upper housing portion, said lower housing portion having a lower housing body extending along a longitudinal axis between a distal and proximal end, and comprising a second chamber therein, said lower housing body having a second opening at said proximal end accessing said second chamber and said second chamber comprises
       an inner and an outer surface and a first plurality of slots extending between said inner surface and said outer surface and
       a ledge extending from said inner surface of said second chamber and having a second plurality of slots aligned with said first plurality of slots;
    a plurality of springs, wherein each spring of said plurality includes a high, low, and mid-range of operation, and wherein said plurality of springs are positioned within at least one of said first and second chambers;
    at least one infusion device; and
    at least one reservoir in fluid communication with said at least one infusion device, said reservoir being positioned adjacent to at least one of said plurality of springs.

12. A fluid delivery device as recited in claim 11 wherein at least one of said plurality of springs is a Belleville spring.

13. A fluid delivery device as claimed in claim 11 further comprising: a shelf, positioned adjacent to said ledge and having a third plurality of slots aligned with said first and second plurality of slots.

14. A fluid delivery device as claimed in claim 13 wherein: said first chamber comprises an inner and an outer surface and having a plurality of tabs extending from said inner surface, said plurality of tabs aligned with said first, second, and third plurality of slots.

15. A fluid delivery device as claimed in claim 14 wherein: said tabs are slidable within said first, second, and third slots between an unactuated and an actuated position, and said plurality of tabs engage at least one of said plurality of springs in said actuated position.

16. A fluid delivery device as claimed in claim 15 wherein: said engaged spring is flexed into at least one of a mid-range and a high-range of operation, and said spring in said mid-range of operation transfers a substantially constant pressure to said adjacent reservoir and forces a substance from said reservoir at a first substantially constant flow rate.

17. A fluid delivery device as claimed in claim 14 further comprising a plurality of bosses extending from said inner surface of said first chamber, wherein said bosses engage at least one of said plurality of springs in an actuated position.

18. A fluid delivery device as claimed in claim 17 wherein: said engaged spring is flexed into at least one of a mid-range and a high-range of operation, wherein said spring in said mid-range of operation transfers a substantially constant pressure to said adjacent reservoir and forces a substance from said reservoir at a second substantially constant flow rate.

19. A fluid delivery device as claimed in claim 14 further comprising: at least one unactuated locking detent and at least one actuated locking detent, each of said detents extending from said inner surface of said first chamber and slidably contacting said outer surface of said second chamber; and at least one unactuated locking recess and at least one actuated locking recess, each said recesses disposed on said outer surface of said second chamber.

* * * * *